United States Patent [19]

Tiede et al.

[11] Patent Number: 5,393,419
[45] Date of Patent: Feb. 28, 1995

[54] ULTRAVIOLET LAMP ASSEMBLY FOR WATER PURIFICATION

[75] Inventors: Merlin G. Tiede, Ada; Dennis J. Kool, Kentwood, both of Mich.; Kenneth E. Lew, Saugas, Calif.

[73] Assignee: Amway Corporation, Ada, Mich.

[21] Appl. No.: 16,140

[22] Filed: Feb. 10, 1993

[51] Int. Cl.⁶ ............................................. C02F 1/32
[52] U.S. Cl. .................................. 210/192; 250/436; 250/437; 250/438; 422/186.3
[58] Field of Search .............. 210/192, 748; 250/435, 250/436, 437, 438; 422/24, 186.3

[56] References Cited

U.S. PATENT DOCUMENTS

| | | | |
|---|---|---|---|
| 1,140,819 | 5/1915 | Henri et al. | |
| 2,719,932 | 10/1955 | Stanworth | 313/112 |
| 3,753,036 | 8/1973 | Roche | 315/60 |
| 3,923,663 | 12/1975 | Reid | 210/443 |
| 4,008,045 | 2/1977 | Free | 250/438 |
| 4,285,032 | 8/1981 | Honda et al. | 362/224 |
| 4,296,328 | 10/1981 | Regan | 250/436 |
| 4,320,324 | 3/1982 | Ariga et al. | 313/493 |
| 4,449,071 | 5/1984 | Yokoyama | 315/53 |
| 4,700,101 | 10/1987 | Ellner et al. | 313/1 |
| 4,769,131 | 9/1988 | Noll et al. | 210/85 |

*Primary Examiner*—Ivars Cintins
*Attorney, Agent, or Firm*—Michael A. Mohr; Jill M. Beckman

[57] ABSTRACT

An apparatus for the treatment of potable water having a substantially cylindrical pressure vessel which houses an ultraviolet light. The pressure vessel is in fluid communication with a filter stage which filters the water before treatment by the ultraviolet light. An ultraviolet lamp assembly sealed within a light permeable sleeve and having a single end cap provided with electrical terminals at one end only is disposed in watertight fashion within the pressure vessel. Downstream from an inlet to the pressure vessel is a deflector/baffle assembly provided to regulate the flow pattern and flow rate of the water within the pressure vessel thereby providing a uniform flow rate to achieve optimum kill rates of bacteria and other living organisms by exposure to the ultraviolet light. The ultraviolet lamp assembly is secured within the pressure vessel by a threaded closure nut which is easily secured or removed by hand.

22 Claims, 5 Drawing Sheets

ULTRAVIOLET LAMP ASSEMBLY FOR WATER PURIFICATION

BACKGROUND OF THE INVENTION

The present invention is generally directed to staged water purification devices in which, during the first stage of purification, potable water passes through a filter for removing particulates and chemicals prior to the water passing on to the second stage in which the water is exposed to ultraviolet light for the killing and sterilization of bacteria and other microorganisms. More particularly, the present invention is directed to a unique baffle and deflector combination provided within an ultraviolet light treatment chamber for control of the flow pattern of water as it passes through the treatment chamber and is exposed to the ultraviolet light source.

Staged water purification devices which are used to purify potable water by passing the water through an ultraviolet light vessel subsequent to passing the water through a filter during a prior stage are known in the art. In designing such devices, it is desirable that during operation of such a device to provide exposure of as much of the water as possible to a source of ultraviolet light while maintaining a continuous, uniform flow of water through the device and adequate water pressure at the spigot. It is also desirable to control exposure time or residency of the water to the ultraviolet light source within the vessel in order to achieve optical kill rates of microorganisms.

Some prior artisans have attempted to achieve such optical results by designing a generally cylindrical ultraviolet water treatment vessel having a water inlet passage on one end of the vessel, a coaxially disposed ultraviolet light tube extending the length of the vessel and a water outlet passage disposed on the end opposite the inlet passage downstream from a filter. In such an ultraviolet water treatment vessel the ultraviolet light bulb in combination with the inside walls of the treatment vessel define a space, parallel to the sides of the cylindrical vessel, through which the water circuits for the inlet passage through the outlet passage wherein the water is exposed to the ultraviolet light radiating from the ultraviolet light bulb before passing on to a filter for further purification.

In such systems, the inlet passage is typically comprised of a tube which is small in diameter relative to the diameter of the cylindrical treatment vessel. One problem that is caused by water entering a relatively large chamber from a relatively small inlet passage tube is that some water typically would short-circuit through the chamber past the ultraviolet light bulb and out the outlet passage without receiving sufficient exposure to ultraviolet light to kill all microorganisms present while another portion of the water will linger in the treatment vessel in the form of small eddy currents creating dead spots. The combination of eddy currents and short-circuiting water results in the undesirable effect of having a portion of the water receiving insufficient exposure time to the ultraviolet light thereby compromising its effectiveness.

Other artisans have attempted to control the flow of water past an ultraviolet light source by passing the water through a helical conduit manufactured of ultraviolet light permeable material and coaxially disposing an ultraviolet light source through the center of the helix. While channeling the water through a helical conduit around an ultraviolet light source is effective in eliminating short-circuits and dead spots in the water path, such conduits have been known to be made of quartz or glass which can shatter and are difficult and costly to manufacture. Depending upon the purity of the quartz or glass, ultraviolet light will solarize impurities in the quartz or glass causing portions of the material to darken thereby compromising its transmission qualities for the transference of ultraviolet light.

In addition to maintaining the rate and pattern of flow of water through the ultraviolet treatment vessel, it is desirable in such water treatment systems to provide easy access to the ultraviolet light element by the user for replacement and inspection. Some prior artisans have provided a user removable housing cover for visually inspecting the wiring and other electric connections to the ultraviolet light element, yet have not provided an easy and safe way in which to remove the light element without first removing and disconnecting a complex array of electrical connections and/or structural components which mount and support the light element within the water treatment system vessel. Thus, it is highly desirable to provide a substantially self-contained ultraviolet light element which requires a minimum of disassembly by the user in order to access and/or remove the element from the water treatment system vessel.

SUMMARY OF THE INVENTION

These problems and others are solved by provision of an elongated, substantially cylindrical ultraviolet treatment pressure vessel having an ultraviolet light source concentrically disposed therein and extending substantially the length thereof and having a unique deflector/baffle system for regulating the flow pattern and flow rate of water through the pressure vessel while the water is exposed to ultraviolet light.

The ultraviolet water treatment system of the present invention is provided with a substantially self-contained ultraviolet light assembly featuring an elongated lamp tube having a single end cap with four electrical connection pins disposed therein, located on a proximate end of the lamp tube. Disposed and fused within the lamp tube at the proximate end is a light filament having two electrical wires extending therefrom and electrically connected to two of the connection pins on the end cap. Disposed within the distal end of the lamp tube is a second filament fused therein having wires extending therefrom along the outside length of the lamp tube and electrically connected to the remaining two pins on the end cap. The entire lamp tube, including a distal portion of the end cap, is sealed within a watertight, elongated, ultraviolet light permeable envelope which insulates the electrical components from exposure to water.

A radially projecting inlet tube is disposed on one end of the pressure vessel and a radially projecting outlet tube is disposed on the opposite end. Adjacent the inlet tube a unique deflector and baffle combination are disposed within the pressure vessel for controlling the flow pattern and the rate at which water passes through. Water entering the pressure vessel from the inlet tube is deflected horizontally by the deflector of the present invention and is thus forced against the cylindrical inner walls of the vessel and continues flowing in a helical pattern. The water is then passed through baffle ports arranged about the periphery of the baffle, thus providing a uniform rate of flow eliminating short circuits and dead spots and thereby allowing the water flow to spiral around and across the length of the coaxial ultraviolet light source before exiting the outlet tube. Thus, the water's exposure to ultraviolet light is maximized and, therefore, optimized by evenly distributing the water passing through the vessel before exiting the outlet tube.

The deflector/baffle system of the present invention can be manufactured from any number of materials which are suitable for exposure to potable water in an ultraviolet environment such as stainless steel or highly ultraviolet light tolerant fluorinated hydrocarbon polymers which are readily available on the market, e.g., PFA, FEP or PTFE Teflon from dupont. However, the preferred material for the deflector/baffle is stainless steel. Further, the deflector/baffle design of the present invention is not excessively complex and is thus not difficult nor expensive to mold or tool for purposes of manufacture.

A proximate portion of the end cap, which remains outside of the envelope, is of a noticeably smaller diameter than the portion of the end cap disposed and sealed within the envelope. The smaller diameter portion of the end cap defines an annular shoulder at the juncture between it and the larger portion of the end cap which is disposed within the envelope.

The pressure vessel, which is spherical on its distal end, features an externally threaded nipple portion at its proximate end wherein the ultraviolet light element is inserted. An internally threaded closure nut is provided which is adapted to be placed over the end cap of the light element and abut the shoulder defined by the juncture between the smaller diameter portion and larger diameter portion of the end cap while allowing the smaller diameter portion of the end cap to extend partially therethrough. The small portion of the end cap is externally threaded and adapted to receive an internally threaded lock nut thereon in order to secure the internally threaded nut upon the shoulder. The internal threads of the closure nut are adapted to be threadingly secured upon the external threads of the pressure vessel nipple portion itself. Thus, with the entire ultraviolet element threadingly secured within the pressure vessel, the four electrical connector pins are exposed allowing a female four-connector pin socket to be secured thereupon which provides an electrical connection to a power source for operation of the ultraviolet light.

In operation, when a user wishes to inspect or remove the ultraviolet light assembly, the user needs only to remove the cover of the housing in which the ultraviolet treatment chamber is disposed, pull the female pin connector socket off of the connector pins in the end cap of the light element, grasp and turn the internally threaded nut closure away from the external threads of the chamber nipple portion and then lift the ultraviolet light assembly out of the pressure vessel in its entirety. The ultraviolet light assembly can then be inspected and replaced simply by reversing the steps described above for removal of the light assembly. This design provides the user with an easy, time-saving access to the ultraviolet light assembly and substantially reduces the danger of component breakage that a more complex disassembly process can entail.

Therefore, one advantage of the present invention is the provision of a substantially self-contained ultraviolet bulb assembly which is easily disconnected, removed and replaced by the average user.

Another advantage of the present invention is the provision of a deflector mechanism in an ultraviolet treatment chamber for deflecting incoming water into a helical pattern as the water flows past an ultraviolet light source within the ultraviolet treatment chamber.

Another advantage of the present invention is the provision of a baffle mechanism within an ultraviolet treatment chamber to provide uniform flow of incoming water as water flows past an ultraviolet light source within the ultraviolet treatment chamber.

A further advantage of the present invention is the provision of the combination of a deflector mechanism and a baffle mechanism within an ultraviolet treatment chamber for deflecting incoming water into a helical pattern and controlling its rate of flow as the water flows past an ultraviolet light source within the ultraviolet treatment chamber.

DETAILED DESCRIPTION OF THE PREFERRED EMBODIMENT

Figure 1:
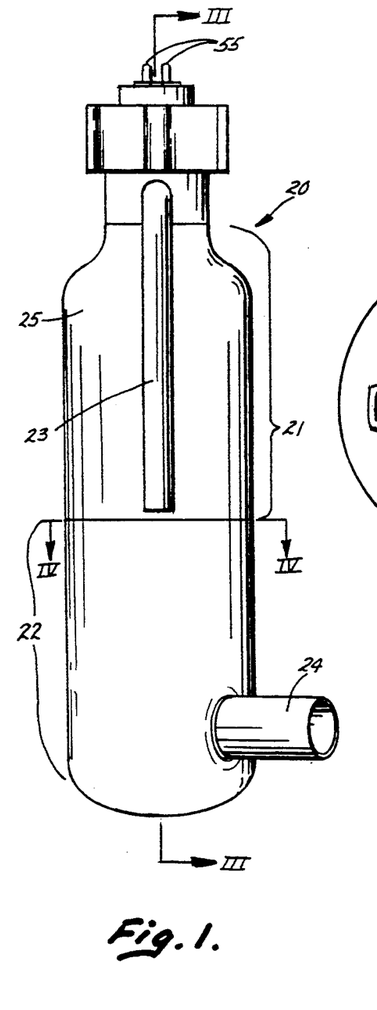
FIG. 1 is an elevational view of an ultraviolet water treatment chamber of the type employing the present invention.
Figure 2:
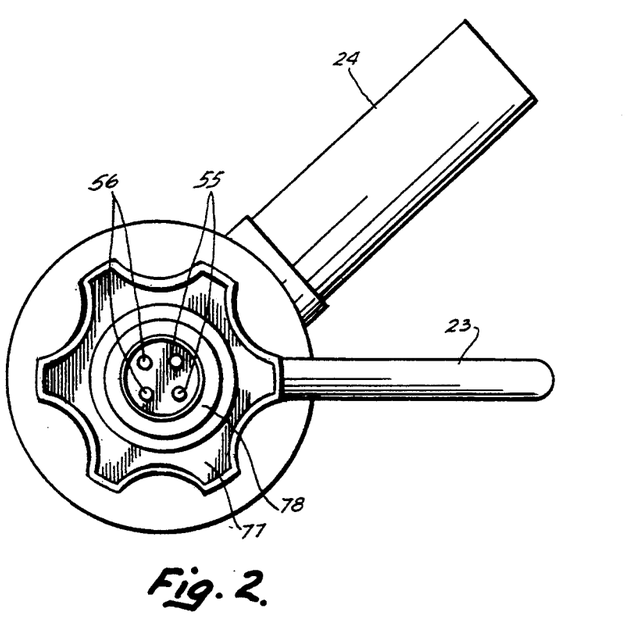
FIG. 2 is a top plan view of the ultraviolet water treatment chamber of FIG. 1.

With reference to the figures and particularly FIGS. 1 and 2, a generally cylindrical ultraviolet water treatment chamber assembly is shown generally at 20. A generally cylindrical pressure vessel 25 of treatment chamber assembly 20 includes a bottom section 22 which is welded, molded or otherwise attached in a watertight fashion to a top section 21.

A water inlet tube 24 is disposed in bottom section 22 extending radially and substantially perpendicular in relation to the axis of pressure vessel 25. An outlet tube 23 is radially disposed in top section 21 having its proximate end extending radially outward and substantially perpendicular to the axis of pressure vessel 25. The outlet tube 23 of this particular embodiment is configured in such a way that a portion of the tube extends parallel to the vertical axis of pressure vessel 25 although this particular outlet tube orientation is not critical in order to practice the best mode of the present invention. However, the ratio of the average diameter of pressure vessel 25 to the distance between the axes of the proximate ends of inlet tube 24 and outlet tube 23 is critical and is preferred to be greater than 2.5:1 and most preferred to be 2.75:1 at an optimum flow rate of 0.8–1.1 gallons per minute to achieve an optimum ultraviolet light contact time averaging 6–9 seconds. Also critical to achieving proper flow within pressure vessel 25 is providing inlet tube 24 with a larger diameter than outlet tube 23. If the diameter of inlet tube 24 is too small relative to outlet tube 23, the velocity of water entering pressure vessel 25 will be too high and portions of the water will short-circuit causing residence time to decrease undesirably. Thus, the ratio of the diameter of inlet tube 24 to outlet tube 23 is preferred to range from 1.5:1–3:1 but is most preferred at 2:1 at an optimum flow rate of 0.8–1.1 gallons per minute to achieve an optimum ultraviolet contact time averaging 6–9 seconds.

Figures 4, 5:
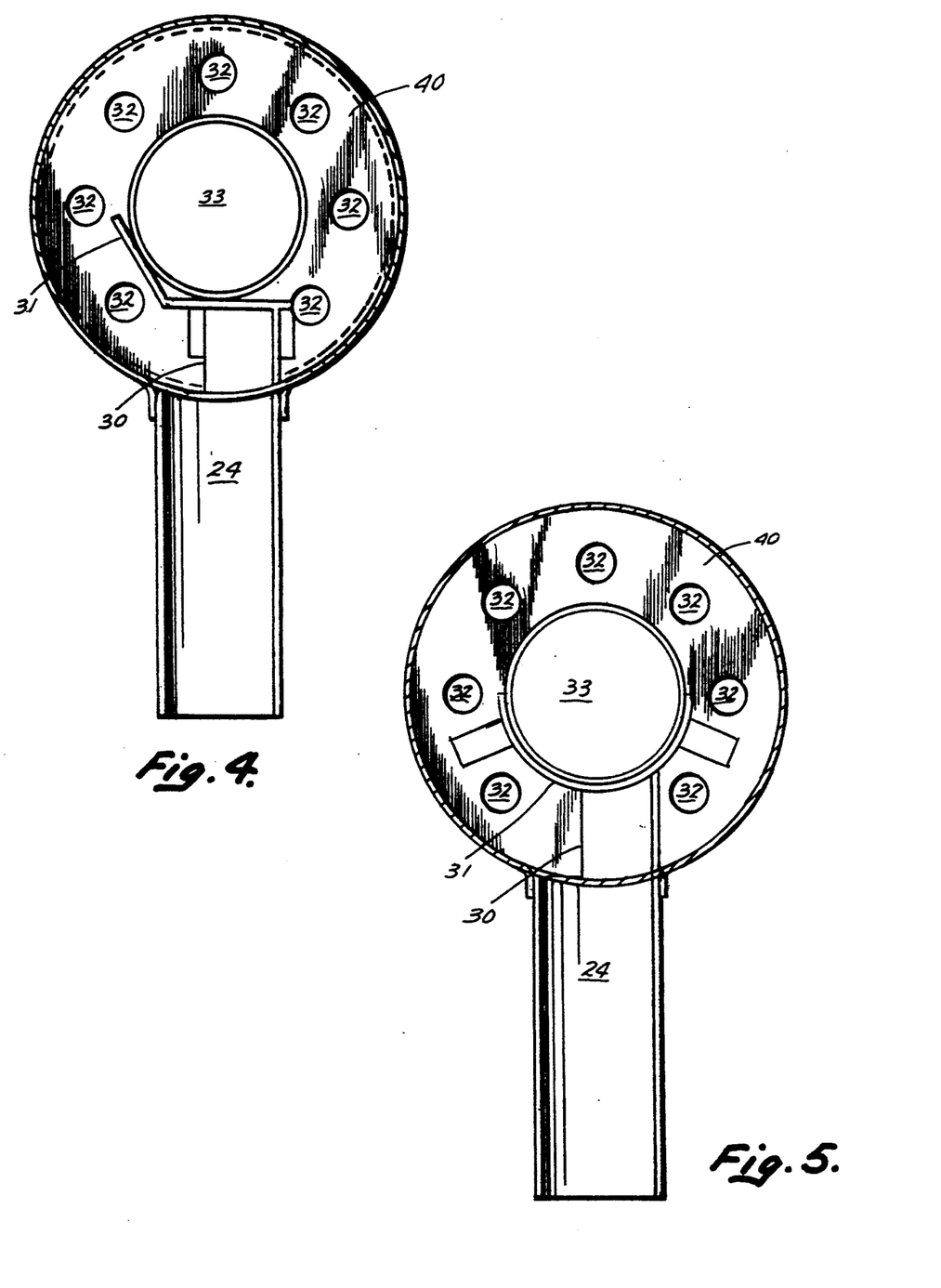
FIG. 4 is a top sectional view of an ultraviolet water treatment chamber showing one preferred embodiment of the deflector/baffle system of the present invention having an angular deflector incorporated therein taken along section lines IV of FIG. 1.
FIG. 5 is a top sectional view of an ultraviolet water treatment chamber showing another preferred embodiment of the deflector/baffle system of the present invention having a semi-circular deflector incorporated therein taken along section lines IV of FIG. 1.
Figure 6:
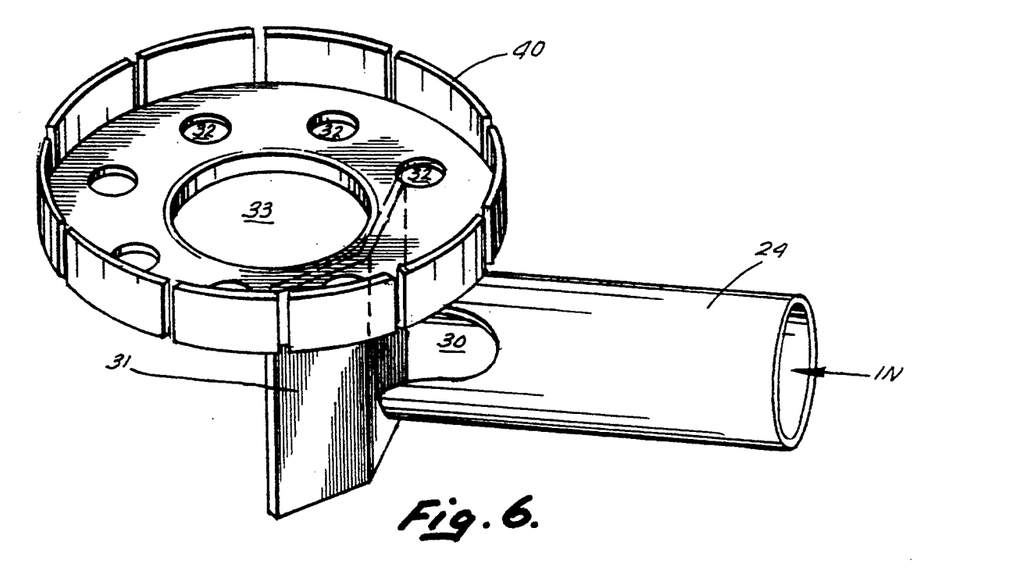
FIG. 6 is a perspective view of one preferred embodiment of the present invention wherein the deflector plate is angular.
Figure 7:
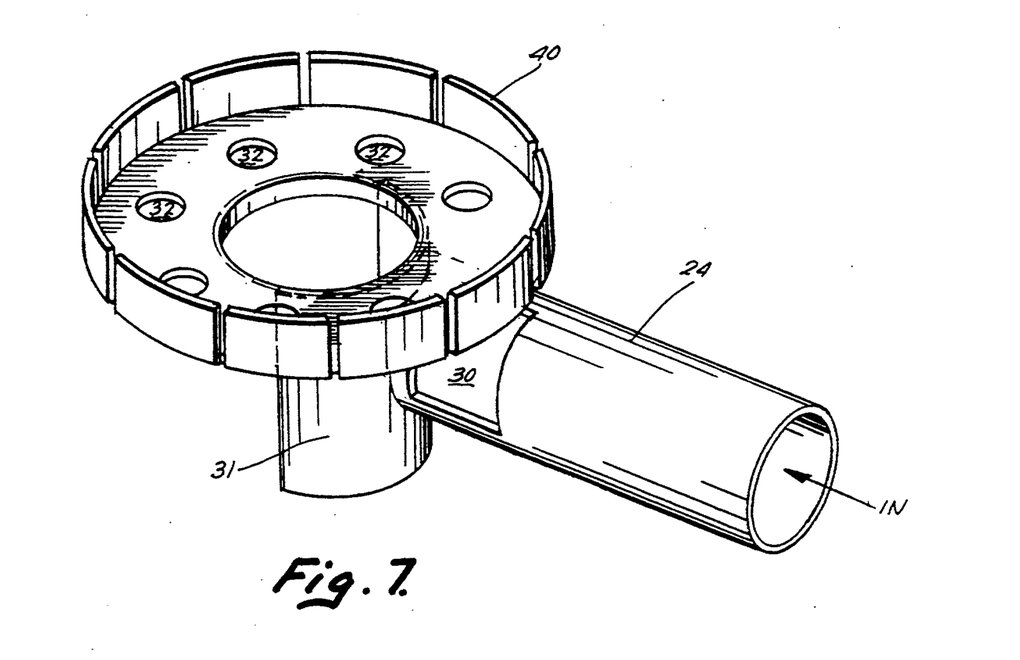
FIG. 7 is a perspective view of another preferred embodiment of the present invention wherein the deflector plate is semi-circular.

In operation, as water enters inlet tube 24 as shown in FIGS. 6 and 7, the water will confront a deflector plate 31 while simultaneously exiting inlet tube 24 through a side discharge port 30 in a clockwise direction following the contour of deflector plate 31. Deflector plate 31 may be angular as shown in FIGS. 4 and 6, or circular as shown in FIGS. 5 and 7. While a circular deflector plate may perform marginally better than one that is angular, a circular piece is more costly to produce. Therefore, preference for either the circular embodiment or angular embodiment of deflector plate 31 must be weighed against cost versus performance concerns. Either embodiment of deflector plate 31 also serves the dual purpose of deflecting the flow of water from side discharge port 30, and providing an ultraviolet shield which prevents ultraviolet light from entering inlet tube 24 via discharge port 30 and affecting any non-metal components nearby.

Continuing with reference to FIGS. 6 and 7, after water is deflected off of deflector plate 31, the water begins a circular path and continues spiraling upward toward a baffle disk 40. Baffle disk 40 has disposed through and around its inner periphery a plurality of symmetrically-spaced, annularly arranged baffle ports 32 which provides back pressure and prevents turbulence thereby avoiding short-circuit paths and providing a uniform flow pattern while also allowing the water to continue in a spiral path. While optimal performance is achieved with a symmetrical arrangement, baffle ports 32 may also be arranged asymmetrically.

Figure 3:
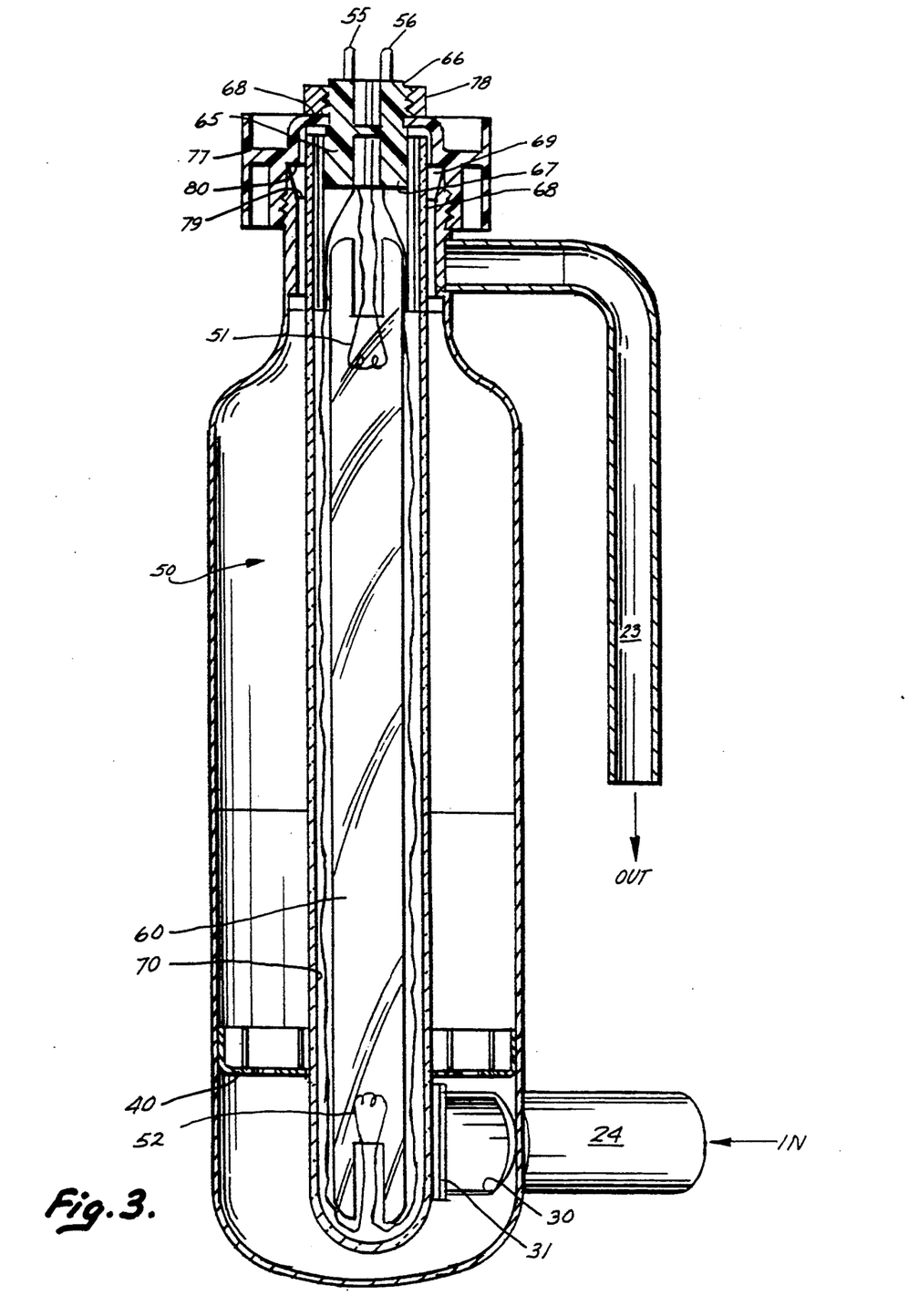
FIG. 3 is a sectional view of an ultraviolet water treatment chamber incorporating the present invention therein taken along section lines III of FIG. 1.

Therefore, functionally, deflector plate 31 causes water flowing inward from side discharge port 30 to begin a clockwise spiraling ascent upward toward baffle disk 40 whereupon baffle ports 32 will provide a uniform rate of flow while substantially maintaining the spiral pattern of the ascending water. Referring to FIG. 3, the water will spiral around an ultraviolet light bulb assembly shown generally at 50 which is centrally located within pressure vessel 25 and extends through, in coaxial relation therewith, baffle disk 40 through a bulb port 33 shown in FIGS. 4, 5, 6 and 7. As shown in FIG. 3, the ascending water is exposed to virtually the entire length of ultraviolet light bulb assembly 50 before it is discharged from outlet port 23 and thereafter through a faucet spigot or the like.

Figure 8:
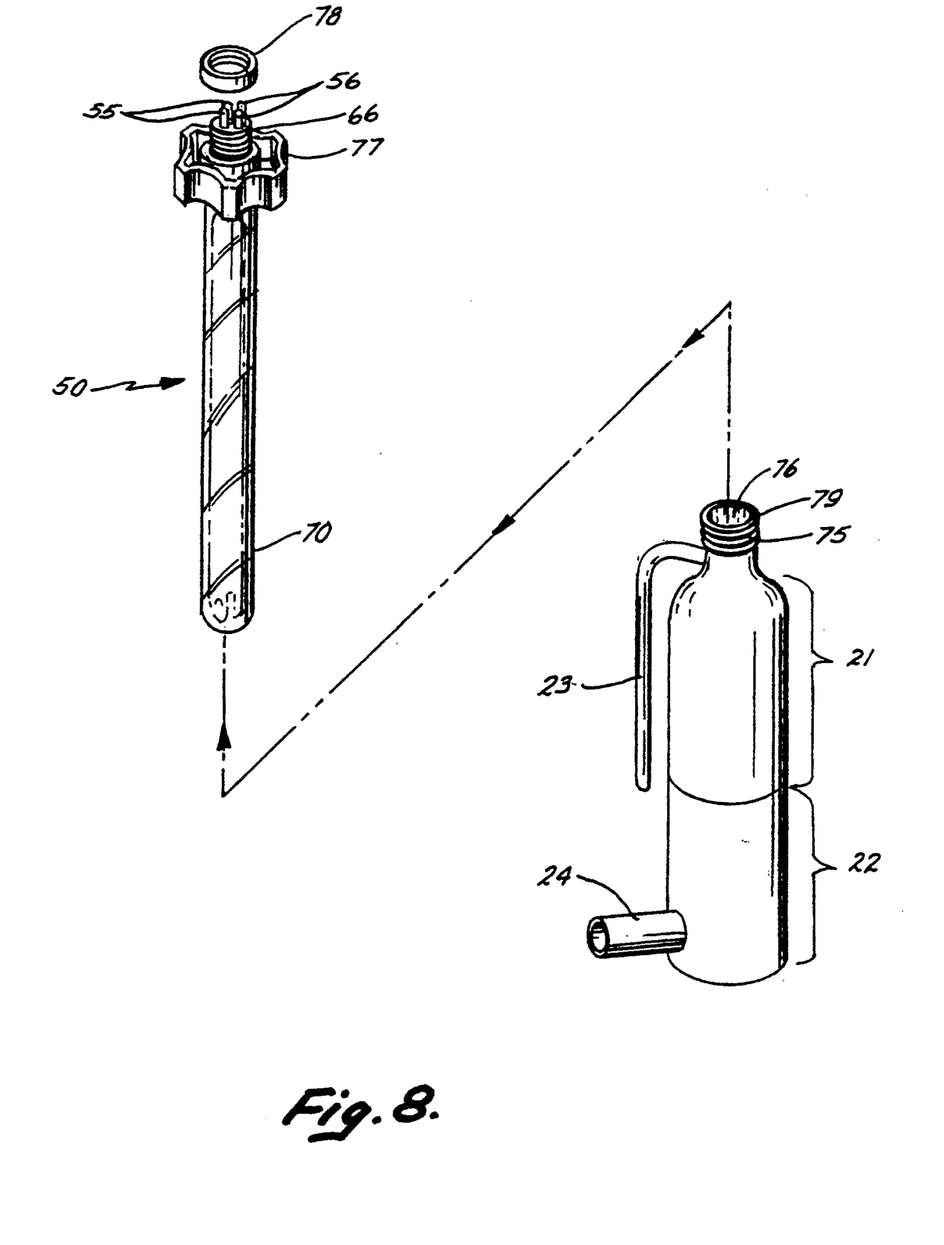
FIG. 8 is an exploded view showing the ultraviolet light assembly with lock nut exposed thereabove and the pressure vessel of the present invention.

As mentioned earlier, the configuration of ultraviolet light bulb assembly 50 shown in FIGS. 3 and 8 is unique in that it is a substantially self-contained assembly. With reference to FIG. 3, the ultraviolet light bulb assembly 50 of the present invention is shown in cross section. Ultraviolet light bulb assembly 50 features an elongated lamp tube 60 having a single stepped end cap 65 having disposed therein and extending therefrom a set of primary electrical connection pins 55 and a set of secondary electrical connection pins 56, shown more clearly in FIG. 2, located at the proximate end of the stepped end cap 65. Disposed within the proximate end of elongated lamp tube 60, and extending from the distal end of stepped end cap 65, is an electrical filament 51 comprising an electrical wire having two ends connected to two primary electrical connection pins 55 in stepped end cap 65. Disposed within the distal end of elongated lamp tube 60 is a second electrical filament 52 fused therein comprised of a single wire having two ends extending therefrom along the outside length of the elongated lamp tube 60 and electrically connected to two secondary pins 56 shown in FIG. 2 which are electrically isolated from pins 55 on stepped end cap 65.

The entire lamp tube 60, including a distal portion 67 of stepped end cap 65, is sealed within a watertight, airtight, elongated, ultraviolet light permeable envelope 70, made preferably from highly purified quartz, which transmits ultraviolet light very well. The proximate portion 66 of stepped end cap 65 which remains outside of the envelope 70 is of a substantially smaller diameter than the distal portion 67 of end cap 65 disposed and sealed within the envelope 70. The proximate end cap portion 66 of the end cap 65 defines an annular shoulder 68 disposed at the juncture between proximate end cap portion 66 and distal end cap portion 67 which is disposed within the envelope 70.

Continuing to refer to FIG. 3 and also FIG. 8, top section 21 of pressure vessel 25 features an externally threaded nipple portion 75 which defines a mouth 76 opening to the interior of pressure vessel 25 into which a substantial portion of ultraviolet light bulb assembly 50 is inserted. It is preferred to dispose outlet tube 23 at externally threaded nipple portion 75 in order to expose water to as much of ultraviolet light bulb assembly 50 as possible since a portion of UV light permeable envelope 70 is disposed within externally threaded nipple portion 70. Further, the narrowing of pressure vessel 25 at externally threaded nipple portion 75 provides sufficient back pressure that the water will tend to flow at a uniform rate across the entire cross section thereof. If outlet tube 23 was disposed further down on top section 21 water would tend to short-circuit upon reaching the outlet. An internally threaded closure nut 77 is adapted to be placed over small end cap portion 66 and abut shoulder 68 while allowing the external threads of small end cap portion 66 to extend partially therethrough. The external threads of small end cap portion 66 are adapted to threadingly receive an internally threaded lock nut 78 to secure closure nut 77 upon shoulder 68 providing a secure fit between pressure vessel 25 and ultraviolet light bulb assembly 50. Alternatively, a C-clip may be successfully substituted for internally threaded lock nut 78, provided that small end cap portion 66 is modified accordingly, with substantially similar results. With particular reference to FIG. 3, an elastomeric O-ring seal 69 is preferably disposed between a peripheral sealing surface 79 adjacent mouth portion 76 and an inner surface 80 of closure nut 77 to provide a watertight seal therebetween. In one preferred embodiment, the threads of the internally threaded nut closure 77 and the externally threaded nipple portion 75 are abrupt, single start coarse pitch threads and, in another preferred embodiment, such threads are adapted to facilitate a 90° turn for closure and removal.

With the entire ultraviolet light bulb 50 threadingly secured within pressure vessel 25, primary and secondary electrical connection pins 55 and 56 are exposed allowing a four-connector female pin socket (not shown) to be secured thereupon, thus providing an electrical connection to a power source (also not shown) for operation of the ultraviolet light.

In operation, when a user wishes to inspect or remove the ultraviolet light bulb assembly 50, the user only needs to remove any housing cover provided with the entire water treatment system revealing the top of the ultraviolet light bulb assembly 50 securely disposed upon pressure Vessel 25. The user then manually pulls the female pin connector socket off of the electrical connector pins 55 and 56, grasps and turns threaded closure nut 77 away from the external threads of nipple portion 75 and then, grasping nut closure 77, lifts the entire ultraviolet light assembly 50 out of pressure vessel 25 in its entirety. Ultraviolet light bulb assembly 50 can then be inspected and replaced simply by reversing the steps described above.

Pressure vessel 25, deflector plate 31, baffle disk 40, inlet tube 24 and outlet tube 23 are preferably manufactured of stainless steel but a variety of ultraviolet light resistant polymer resins may be used to achieve similar results. Envelope 70 of light assembly 50 is preferably made of quartz as quartz has been found to provide optimal ultraviolet permeability for optimal microorganism kill rates.

Thus, a highly efficient, compact and easily maintained ultraviolet water treatment module is obtained. Such a module can be installed as the ultraviolet radiation treatment stage of virtually any domestic potable water treatment system employing a filter made from paper, fabric, granulated or block carbon, activated granulated or block carbon, reverse osmosis or combinations thereof. The ultraviolet treatment system of the present invention is most preferably employed in a domestic potable water treatment system which first filters water through an activated pressed carbon block water filter employing a fabric/mesh pre-filter.

Although illustrative embodiments Of the present invention have been described herein with reference to the accompanying drawings, it is to be understood that the invention is not limited to those precise embodiments, and that various other changes and modifications may be effected therein by one skilled in the art without departing from the scope or spirit of the invention.

The embodiments of the invention in which an exclusive property or privilege is claimed are defined as follows:

1. In an apparatus for the treatment of water, an elongated substantially cylindrical pressure vessel having a longitudinal axis comprising:
   a distal end and a proximate end;
   said proximate end comprising a circumferential mouth across the diameter thereof;
   an ultraviolet light coaxially disposed through said circumferential mouth into said vessel and extending substantially the length thereof;
   an inlet tube disposed in said distal end;
   an outlet tube disposed in said proximate end;
   said inlet tube having a larger diameter than said outlet tube;
   said inlet tube comprising a discharge end and a side discharge port;
   said inlet tube being spaced apart from said outlet tube by a distance at least 2.5 times and no greater than 2.75 times the average diameter of said pressure vessel;
   a means for deflecting water disposed adjacent said side discharge port adapted to deflect water radially from said side discharge port in one direction only;
   a baffle comprising a horizontal disk, said disk containing a plurality of baffle ports; and
   whereby water entering said pressure vessel from said inlet tube flows through said side discharge port and is directed by said deflector means radially in one direction only and said baffle through said baffle ports and continuing in a spiral path around said ultraviolet light and out of said outlet tube.

2. The apparatus of claim 1 wherein said baffle is disposed in a perpendicular plane with respect to the longitudinal axis of said vessel and extends across the entire cross section between said inlet tube and said outlet tube.

3. The apparatus of claim 1 wherein said baffle ports provide a uniform rate of water flow thereby maximizing water exposure to said ultraviolet light for the sterilization of microorganisms in said water.

4. The apparatus of claim 1 wherein said outlet tube is disposed at a portion of said pressure vessel substantially narrower than said distal end.

5. The apparatus of claim 1 wherein said baffle ports have axes in parallel relationship with respect to the longitudinal axis of said baffle and are disposed radially therefrom.

6. The apparatus of claim 1 wherein a terminus of a first end of said ultraviolet light protrudes slightly beyond said mouth of said vessel.

7. The apparatus of claim 1 wherein said deflector means is arcuate in shape.

8. The apparatus of claim 1 wherein said deflector means is angular in shape.

9. The apparatus of claim 1 wherein said baffle ports are symmetrically disposed about the axis of said baffle.

10. The apparatus of claim 1 wherein said baffle ports are asymmetrically disposed about the axis of said baffle.

11. The apparatus of claim 1 wherein said pressure vessel, said deflector means, said baffle, said inlet tube and said outlet tube are manufactured of stainless steel.

12. An apparatus for the treatment of water comprising:
   an elongated substantially cylindrical pressure vessel having a longitudinal axis comprising a distal end and a proximate end;
   said proximate end comprising a circumferential mouth across the diameter thereof;
   an ultraviolet light disposed within said pressure vessel coaxially with respect to the longitudinal axis of said pressure vessel and extending substantially the length thereof, whereby the terminus of a first end of said ultraviolet light protrudes slightly beyond said mouth;
   said distal end comprising an inlet tube disposed adjacent a second end of said ultraviolet light;
   said proximate end comprising an outlet tube disposed adjacent said first end of said ultraviolet light;
   said inlet tube having a larger diameter than said outlet tube;
   said inlet tube being spaced apart from said outlet tube by a distance at least 2.5 times and no greater than 2.75 times the average diameter of said pressure vessel;

whereby said vessel, said inlet tube and said outlet tube provide a continuous passage therethrough;

said inlet tube further comprising a discharge end and a side discharge port;

a means for deflecting water disposed within said vessel adjacent said discharge port adapted to deflect water radially from said side discharge port in one direction only;

said deflector means being further adapted to define a substantially arcuate passage of fluid discharged from said discharge port in only one direction commencing on a substantially perpendicular plane with respect to the longitudinal axis of said vessel and spiraling in a direction toward said outlet tube following a substantially parallel plane with respect to the longitudinal axis of said vessel;

a baffle for regulating flow of fluid within said passage disposed within said vessel downstream from said inlet tube on a substantially perpendicular plane with respect to the longitudinal axis of said vessel and extending substantially across the entire cross section thereof between said inlet tube and said outlet tube;

said baffle comprising a disk having a longitudinal axis disposed in coaxial relationship with the longitudinal axis of said vessel;

said baffle further comprising a plurality of longitudinal baffle ports having axes in parallel relationship with respect to the longitudinal axis of said baffle and disposed radially therefrom; and whereby said baffle ports provide a plurality of fluid passages within said passage for directing fluid flowing therethrough, to and around said ultraviolet light and for providing uniform rate of fluid flow thereby optimizing fluid contact time to ultraviolet light for the sterilization of microorganisms laden therein.

13. The apparatus of claim 12 wherein said ultraviolet light comprises an elongated lamp tube.

14. The apparatus of claim 13 further comprising a single end cap.

15. The apparatus of claim 14 wherein said end cap comprises a proximate end and a distal end, said proximate end having disposed therein and extending therefrom a set of primary electrical connector pins and a set of secondary electrical connector pins.

16. The apparatus of claim 15 further comprising on said proximate end located distally from said primary electrical connector pins, two electrical leads, each of said leads having one end electrically connected to said primary connector pins and having another end connected to an electrical filament and on said distal end a second set of filament leads disposed and fused therein with one end of each lead extending along an outside surface of said elongated lamp tube in the direction of said single end cap with each of said leads connected to said secondary connector pins.

17. The elongated lamp tube of claim 16 wherein said distal portion of said single end cap and said elongated lamp tube and said first filament leads and said second filament leads are sealingly disposed within an ultraviolet light permeable closed-ended sleeve.

18. An apparatus for the treatment of water comprising:

a substantially cylindrical elongated pressure vessel having inlet and outlet tubes disposed adjacent opposing ends of said pressure vessel in fluid communication therewith;

said inlet tube having a larger diameter than said outlet tube;

said inlet tube being spaced apart from said outlet tube by a distance of at least 2.5 times and no greater than 2.75 times the average diameter of said pressure vessel;

said inlet tube comprising a side discharge port;

an ultraviolet light disposed within said pressure vessel extending substantially the length thereof;

said ultraviolet light comprising an elongated lamp tube;

said lamp tube having disposed therein a single end cap;

said end cap comprising a proximate portion and a distal portion;

said proximate portion of said end cap having disposed therein and extending therefrom a set of primary electrical connector pins and a set of secondary electrical connector pins;

said lamp tube comprising on its proximate end and located distally from said primary connector pins two electrical leads each having one end electrically connected to said primary connector pins and having the other end connected to an electrical filament;

said lamp tube further comprising on its distal end a second set of filament leads disposed and fused therein with one end of each lead extending along the outside surface of said lamp tube in the direction of said single end cap with each of said leads connected to said secondary connector pins; and said distal portion of said single end cap and said lamp tube and said first filament leads and said second filament leads being sealingly disposed within an ultraviolet light permeable closed-ended sleeve.

19. The apparatus of claim 18 wherein said ultraviolet light is secured within said pressure vessel by a threaded closure nut.

20. The apparatus of claim 19 wherein said threaded closure nut is adapted with coarse threads to facilitate a 90° turn closure.

21. The apparatus of claim 18 wherein said ultraviolet light permeable closed-ended sleeve is made from quartz.

22. An apparatus for the treatment of water comprising:

an elongated substantially cylindrical pressure vessel having a longitudinal axis comprising a distal end and a proximate end;

said proximate end comprising a circumferential mouth across the diameter thereof;

an ultraviolet light disposed within said pressure vessel coaxially with respect to the longitudinal axis of said pressure vessel and extending substantially the length thereof, whereby the terminus of a first end of said ultraviolet light protrudes slightly beyond said mouth;

said distal end comprising an inlet tube disposed adjacent a second end of said ultraviolet light;

said proximate end comprising an outlet tube disposed adjacent said first end of said ultraviolet light;

said inlet tube having a larger diameter than said outlet tube;

said inlet tube being spaced apart from said outlet tube by a distance at least 2.5 times and no greater than 2.75 times the average diameter of said pressure vessel;

whereby said vessel, said inlet tube and said outlet tube provide a continuous passage therethrough;

said inlet tube further comprising a discharge end and a side discharge port;

a means for deflecting water disposed within said vessel adjacent said discharge port;

said deflector means being adapted to define a substantially arcuate passage of fluid discharged from said discharge port radially in only one direction commencing on a substantially perpendicular plane with respect to the longitudinal axis of said vessel and spiraling in a direction toward said outlet tube following a substantially parallel plane with respect to the longitudinal axis of said vessel;

a baffle for regulating flow of fluid within said passage disposed within said vessel downstream from said inlet port on a substantially perpendicular plane with respect to the longitudinal axis of said vessel and extending substantially across the entire cross section thereof between said inlet tube and said outlet tube;

said baffle comprising a disk having a longitudinal axis disposed in coaxial relationship with the longitudinal axis of said vessel;

said baffle further comprising a plurality of longitudinal baffle ports having axes in parallel relationship with respect to the longitudinal axis of said baffle and disposed radially therefrom;

whereby said baffle ports provide a plurality of fluid passages within said passage for directing fluid flowing therethrough, to and around said ultraviolet light and for providing a uniform rate of fluid flow thereby maximizing fluid exposure to said ultraviolet light for the sterilization of microorganisms laden therein;

said ultraviolet light comprising an elongated lamp tube;

said lamp tube having disposed therein a single end cap;

said end cap comprising a proximate portion and a distal portion;

said proximate portion having disposed therein and extending therefrom a set of primary electrical connector pins and a set of secondary electrical connector pins;

said lamp tube comprising on its proximate end and located distally from said primary electrical connector pins two electrical leads each having one end electrically connected to said primary connector pins and having the other end connected to an electrical filament;

said lamp tube further comprising on its distal end a second set of filament leads disposed and fused therein with one end of each lead extending along the outside surface of said lamp tube in the direction of said single end cap with each of said leads connected to said secondary connector pins; and said distal portion of said single end cap and said lamp tube and said first filament leads and said second filament leads being sealingly disposed within an ultraviolet light permeable closed-ended sleeve.

* * * * *

UNITED STATES PATENT AND TRADEMARK OFFICE
CERTIFICATE OF CORRECTION

PATENT NO.   : 5,393,419
DATED        : February 28, 1995
INVENTOR(S)  : Merlin G. Tiede et al.

It is certified that error appears in the above-identified patent and that said Letters Patent is hereby corrected as shown below:

Column 1, line 33;
  "optical" should be --optimal--.

Column 1, line 42;
  "for" should be --from--.

Signed and Sealed this

Twenty-fifth Day of June, 1996

Attest:

BRUCE LEHMAN

Attesting Officer   Commissioner of Patents and Trademarks